United States Patent [19]

Blackmore

[11] Patent Number: 4,592,338
[45] Date of Patent: Jun. 3, 1986

[54] CALF SCREENING

[75] Inventor: David J. Blackmore, Littleport, England

[73] Assignee: Ab-Ag Laboratories Limited, Cambridgeshire, England

[21] Appl. No.: 758,107

[22] Filed: Jul. 23, 1985

[30] Foreign Application Priority Data

Jul. 24, 1984 [GB] United Kingdom ................. 8418828

[51] Int. Cl.$^4$ ............................................. A61M 1/03
[52] U.S. Cl. ...................................... 128/1 R; 119/1; 436/547
[58] Field of Search ........................ 128/1 R, 763–768; 119/1; 436/517, 547; 424/101

[56] References Cited

U.S. PATENT DOCUMENTS

| | | | |
|---|---|---|---|
| 4,365,632 | 12/1982 | Kortum | 128/1 R |
| 4,402,940 | 9/1983 | Nose et al. | 128/1 R |
| 4,464,166 | 8/1984 | Delson | 128/1 R |

*Primary Examiner*—John D. Yasko
*Attorney, Agent, or Firm*—Renner, Otto, Boisselle & Lyon

[57] ABSTRACT

A screening system for assessing passive immunity in a multiplicity of calves involves collecting a blood sample from each of a multiplicity of calves; establishing and maintaining a correlation between each blood sample and the respective calf; contacting a predetermined volume of each blood sample with a predetermined amount of an anti-IgG under assay conditions which will visualize the immunoreaction between Ig in the sample and the anti-IgG; monitoring the immunoreaction for each contacted blood sample to determine the presence ("positive result") or absence ("negative result") of a preset level of immunoglobulin G in each blood sample; and identifying the calves which show a positive result and/or the calves which show a negative result.

10 Claims, 2 Drawing Figures

CALF SCREENING

BACKGROUND OF THE INVENTION

The present invention relates to calves, and in particular to the screening of calves for passive immunity.

Newly born calves can only acquire passive immunity to disease through uptake of immunoglobulin (Ig) from colostrum. This transfer of colostral Ig is only possible within the first day of the life of the calf. Termination of the intestinal permeability occurs spontaneously at a progressively increasing rate after 12 hours postpartum. The amount of Ig transfer varies widely, and it is recognized that up to 30% of calves do not acquire adequate passive immunity. The resultant low Ig concentration is associated with a high rate of morbidity and mortality in the neonatal calf.

OBJECTS OF THE INVENTION

The present invention has as its object a quick and easy way to assess levels of passively acquired calf immunity, particularly by a mass screening procedure applicable to large-scale use at markets or other locations where an on-the-spot system would be very useful. A related object is to provide a system for monitoring of neonatal calves allowing problem calves to be identified within minutes.

SUMMARRY OF THE INVENTION

To this end, the present invention provides a screening system for assessing passive immunity in a multiplicity of calves, the system involving:

(a) collecting a blood sample from each of a multiplicity of calves;

(b) establishing and maintaining a correlation between each blood sample and the respective calf;

(c) contacting a predetermined volume of each blood sample with a predetermined amount of an anti-IgG under assay conditions which will visualize the immunoreaction between Ig in the sample and the anit-IgG;

(d) monitoring the immunoreaction of each contacted blood sample to determine the presence ("positive result") or absence ("negative result") of a preset level of immunoglobulin G in each blood sample; and (e) identifying the calves which show a positive result and/or the calves which show a negative result.

In a typical situation, the present test system can be carried out on-the-spot on a large scale and results may be known within ten minutes of the blood sample being taken. Thus, for example, the system is well suited for adoption at a market or other point of sale, at a large calf rearing unit, or any other location where calves are kept together temporarily or permanently. The present system is particularly suited for testing at least 10, more usually at least 20 or 30 calves at one site. In skilled hands, it is possible to test typically 100 calves per hour.

The present invention employs rapid visualization of the immunoreaction between bovine IgG and anti-bovine IgG. Suitable assay conditions for visualizing the immunoreaction are those which allow a test result to be obtained within a suitably short period of time, such as 1 to 30 minutes. For preference, the assay conditions are chosen to give a test result within 10 or better still within 5 minutes.

PREFERRED EMBODIMENTS OF THE INVENTION

In general, there are various assay procedures which can be adopted for the present invention. A preferred approach involves testing for a preset level of between 1 and 15 g IgG/l in the blood sample (assessed on the basis of whole blood, and allowing for any dilution). A cut-off level of 4 to 12 g IgG/l, especially around 10 g IgG/l is usually appropriate, though other cut-off values can be adopted, if desired.

By way of illustration, the present system can involve effecting the immunoreaction in the presence of a particulate indicator. A suitable particulate indicator can easily give physical visualization of the immunoreaction through agglutination. Thus, in one specific embodiment, the invention employs conditions corresponding to a latex agglutination assay. In a latex agglutination assay, the antibody or antigen is loaded on to fine particles. When the antibody/latex particles come in to contact with the corresponding immunoreactant, the immunoreation occurs, leading to agglutination or clumping of the latex particles. A direct or indirect agglutination assay is possible. The present invention can employ the available latexes, such as a 10% suspension of polystyrene particles of 0.5 micron diameter, though the nature of the latex is not critical.

In a modification of a conventional latex agglutination assay, use is made of an unreported finding that it is not necessary for the anti-IgG to be coated on to the indicator particles before the immunoreaction takes place. Thus, the present assay can be achieved by addition of the indicator particles while the immunoreaction is taking place.

The nature of the particulate indicator is not particularly critical, though in general it will comprise inert inorganic or organic particles of relatively uniform small size. Powdered charcoal dust, colloidal charcoal, powdered chalk dust, and polystyrene latex particles represent typical materials. The indicator particles preferably have a size of up to several microns, with a size of up to 1 micron, more especially up to 0.7 micron being particularly preferred.

It can readily be arranged that a positive result occurs within a convenient time when the concentration of IgG is at the specified preset level corresponding to a positive result. If needed, a reaction accelerator can be included in the assay system. The nature of the immunoreaction accelerator is not particularly critical, though in general it will comprise a dissolved organic or inorganic substance. Polyethylene glycol ("PEG") is currently the preferred accelerator, more especially a PEG with a molecular weight of at least several thousand. A PEG 6000 is particularly preferred.

The nature and amount of the accelerator represent useful variables in the devising of assay kits and procedures in accordance with this invention. Thus, for example, the accelerator can be used simply to give a test result within a shorter time, or to allow a variation in the remainder of the reaction system while still achieving a previous test time. As a further possibility, the amount of the accelerator can be varied from batch to batch in order to give a constant test time for a kit despite batch variations in the anti-IgG.

The present invention further provides a kit for mass screening of calves to assess passively acquired immunity. The kit comprises a stock of anti-IgG reagent; means for obtaining separate blood samples from a multiplicity of calves; means for ensuring appropriate dilution of each blood sample to give diluted samples of concentration required for immunoreaction with the reagent to take place under standardized assay conditions; and means for establishing and maintaining a correlation between each blood sample and the respective calf.

The inclusion of the means for ensuring appropriate dilution, such as a supply of diluent containers and a displacement pipette, enables the level of diluent and/or the volume of blood to be pre-selected in accordance with the strength of the stock of anti-IgG reagent. The use of the dilution means is particularly advantageous in that it can also help to ensure consistent results despite batch variations in the production of the anti-IgG reagent. For each production run, the concentration of the stock solution of particles and the degree of dilution can be varied to give the same correlation for agglutination or other immunoreaction.

The production of the anti-IgG can readily be achieved using known techniques, for example by raising the antibodies in sheep. In practice, to produce a preferred reagent that can be used consistently for the measurement of IgG, the sheep or other antibody is selected from a suitable source, carefully titrated, purified, and diluted so that the time taken for the assay falls within a practical period. Furthermore, dilution of the sample that is mixed with reagent should be carefully controlled so that the ratio of IgG to reagent is constant and the assay result falls within a fixed time frame.

These two criteria necessitate titration and determination of individual dilution of volumes for each batch of reagent that is prepared. The appropriate dilution can be ensured for example by appropriate variation in the volume of blood or the volume of diluent for the blood: by either way the concentration of the diluted blood is appropriate to the particular concentration of the batch of anti-IgG reagent.

In addition the timing of reaction and standardisation of reagents should be undertaken using the same equipment as that constituting the test kit. It is also expedient to take steps to prevent cross contamination.

EXAMPLE OF THE INVENTION

Figure 1:
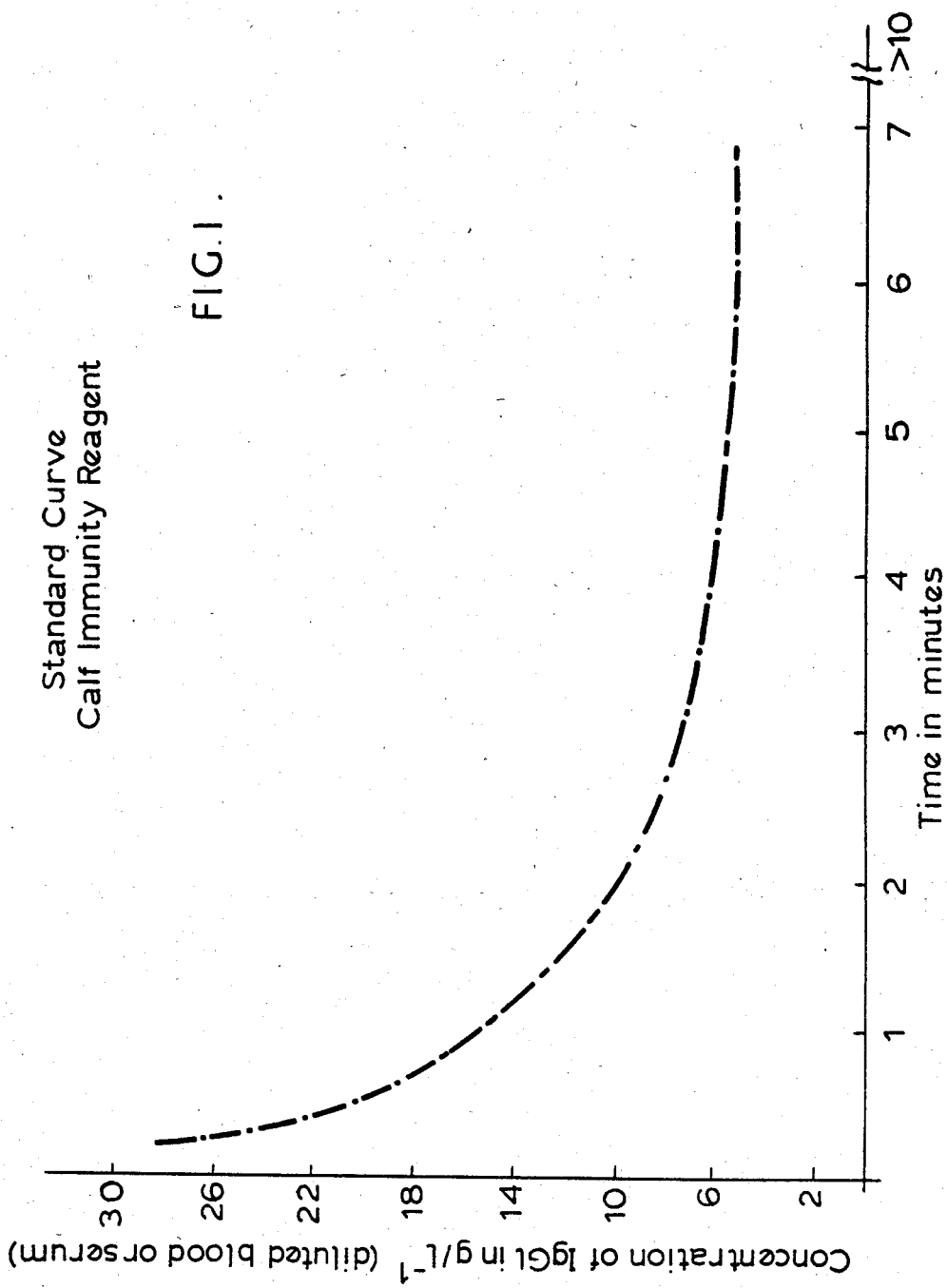
FIG. 1 is a typical standard curve for the agglutination time in the present test method.

Four sheep which had previously been sensitised to a purified calf $IgG_1$ sample were boosted with an intramuscular injection of an emulsion of equal volumes of Freunds Complete Adjuvant and a calf $IgG_1$ solution.

Ten days later the animals were bled from the jugular vein and serum obtained from the clotted sample.

The avidity of the antiserum was assessed by immunoprecipitation with purified $IgG_1$ and the specificity of the antiserum by immunoelectrophoresis against calf plasma samples. It was found necessary to adsorb the antisera against IgG-free bovine sera overnight at 4° C.

The sheep globulins were precipitated with ammonium sulphate, the supernatant discarded, the precipitate washed with ammonium sulphate solution and redissolved in borate buffer.

Latex (10% polystyrene solids) was added to a final concentration of 4% and bovine serum albumin to give a total protein concentration of 8 $gl^{-1}$. The suspension was left overnight at 4° C. and the pH of the reagent adjusted to around 8 with 1M sodium hydroxide. The reagent was then assayed against dilutions of calf sera with pre-determined oncentrations of $IgG_1$.

The curve obtained for times of agglutination of the reagent with 1/100th dilutions of equine sera is shown in the drawing. From this curve it is possible to semi-quantitate the concentration of $IgG_1$ in test samples from the time of agglutination.

Given any particular batch of anit-$IgG_1$/latex, it is a simple matter by experimental determination to compensate for strength variations and ensure appropriate dilution of a blood sample such that the agglutination times correspond to the standard curve. For this particular example, the amount of diluent was pre-set at 2 ml and the appropriate amount of blood was obtained using a displacement pipetter delivering 20 microliter.

The present invention can be adopted for repeated large-scale screenings, and to this end the skilled veterinarian will ordinarily require two kinds of equipment, made up of fixed and consumable portions. The fixed components will suitably comprise a suspension mixer for gentle rotational agitation of samples during testing, one or more blood tube collection racks, a displacement pipette for pipetting a preset volume of each blood sample after dilution, and one or more mixer racks for holding consumable components during preparation of each test sample. Kits can then be produced of the consumables, each kit suitably containing a supply of the following components:

(i) blood collection tubes for collecting blood samples from calves, preferably in the form of evacuated blood collection tubes such as those available under the registered trade mark "VACUTAINER";

(ii) marked capillary tubes for drawing up and transferring a preset volume of each blood sample;

(iii) pipette tips for the displacement pipette;

(iv) diluent tubes each containing a preset volume of aqueous diluent, optionally further containing a reaction accelerator such as PEG 6000, and intended to receive a preset volume of each blood sample;

(v) anti-$IgG_1$/latex reagent;

(vi) positive and negative controls;

(vii) test cards marked out with test areas;

(viii) mixing rods;

(ix) a set of labels for identifying samples and thereby maintaining the correlation between the samples and the test results; and (x) a record sheet or other means for recording the test results.

If desired, the displacement pipette and the components (ii) and (iii) can be replaced by a sampler/diluter such as a bottle top dispenser diluter. The diluent tubes (iv) will then be supplied empty, since the sampler/diluter can carry out in one operation the drawing up of the preset volume of the blood sample and the dilution.

The kits can also include marker pens for marking up the test results on the test cards and the record sheets. In order to authenticate the test results, certificates can further be included in the kits for completion by a user.

If desired, the components (vii) and (x) can be replaced by a combined test card and record sheet.

The test card can usefully be designed for superposition on the mixer rack employed for the preparation of samples. To this end, the test card can include apertures for the blood collection tubes, diluent tubes and pipette tips, such that each blood collection tube, diluent tube and pipette tip can be associated with a respective test area. Furthermore, the test card preferably includes for each test area a corresponding area on which the test result may be marked.

The record sheet is suitably printed to allow easy maintenance of the correlation between the individual calves and the corresponding test results.

There are preferably four labels for each blood sample: one is for the blood collection tube, one is for the diluent tube, one is for the test chart, and one is for the record sheet. If a combined test chart and record sheet is employed then three labels will suffice to maintain the correlation between calf and test result.

Figure 2:
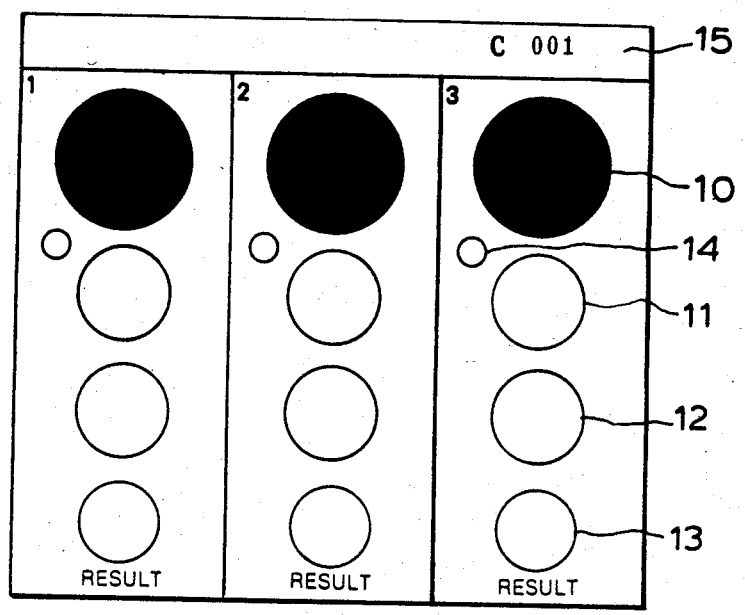
FIG. 2 is part of a test plate for use in the present test method.

Kits were made up using a test card as partially shown in FIG. 2 of the accompanying drawings. The test card is intended for testing of 20 calves. The layout is shown for the first three calves, though all are the same. The large black circle represents the test area 10 for the calf. There are then two holes 11, 12 below to retain sample tubes, one for whole blood and one for diluted blood. The circle 13 at the bottom for each calf is for marking of the result, typically with a green or a red mark to denote a satisfactory or a problem calf, respectively. The smaller hole 14 to the left is to retain a disposable pipette tip. A test reference number 15 for the batch of tests is usually applied to the test card.

The kits can be used in the following general manner:

Operating Procedure

1. The ear tag number for each calf is marked on the record sheet and a label placed in correspondence with the number.
2. Blood from each calf is collected in a like labelled collection tube.
3. The blood collection tubes are temporarily held on the mixer rack.
4. Using the displacement pipette, an aliquot of each blood sample is added to a correspondingly labelled blood dilution tube.
5. An aliquot of each diluted blood sample is added to a respectively labelled test area on the test plate, and the diluent tube is held on the plate adjacent the test area.
6. A preset volume of reagent is added to each test area and mixed well, and the positive and negative controls are set up.
7. The card is left for two minutes.
8. The card is placed on the suspension mixer to effect gentle agitation for a timed period, typically 10 minutes.
9. Each test area is inspected, and results are noted on the data chart. Agglutination indicates a positive result, while the absence of agglutination indicates a negative result, If desired, the calves with negative results can be tested again.

I claim:

1. A screening system for assessing passive immunity in a multiplicity of calves on the basis of assay results for blood samples, said system involving:
   (a) collecting a blood sample from each of a multiplicity of calves;
   (b) establishing and maintaining a correlation between results for each blood sample and the respective calf;
   (c) contacting a predetermined volume of each blood sample with a predetermined amount of an anti-IgG, said contacting being effected under assay conditions which will visualize immunoreaction between Ig in said sample and said anti-IgG;
   (d) monitoring said immunoreaction for each contacted blood sample to determine the presence ("positive result") or absence ("negative result") of a preset level of immunoglobulin G in each blood sample; and
   (e) identifying calves which show a positive result and/or the calves which show a negative result.

2. The screening system of claim 1, wherein at least 10 calves are tested.

3. The screening system of claim 1, wherein said assay conditions are selected to give a result within 10 minutes.

4. The screening system of claim 1, wherein said preset level is from 4 to 12 g IgG/l in the sample, calculated on the basis of whole blood.

5. The screening system of claim 1, wherein said immunoreaction is visualized using a particulate indicator.

6. The screening system of claim 5, wherein said particulate indicator is a latex.

7. The screening system of claim 5, wherein a reaction accelerator is included in said assay system.

8. A kit for mass screening of calves to assess passively acquired immunity, said kit comprising
   a stock of anti-IgG reagent;
   means for obtaining separate blood samples from a multiplicity of calves;
   means for ensuring appropriate dilution of each blood sample to give diluted samples of a required concentration, said required concentration being the concentration required for immunoreaction with the reagent to take place under standardized assay conditions; and
   means for establishing and maintaining a correlation between each blood sample and a respective calf.

9. A kit for mass screening of calves to assess passively acquired immunity, the kit comprising a supply of the following components:
   (i) blood collection tubes for collecting blood samples from calves;
   (ii) marked capillary tubes for drawing up and transferring a preset volume of each blood sample;
   (iii) pipette tips for a displacement pipette;
   (iv) diluent tubes each containing a preset volume of aqueous diluent and intended to receive a preset volume of each blood sample;
   (v) anti-IgG$_1$/latex reagent;
   (vi) positive and negative controls;
   (vii) test cards marked out with test areas;
   (viii) mixing rods;
   (ix) a set of labels for identifying samples and thereby maintaining the correlation between the samples and the test results; and
   (x) a record sheet or other means for recording the test results.

10. The kit of claim 9 when further supplemented with a suspension mixer, blood collection rack, displacement pipette and mixer rack.

* * * * *